(12) United States Patent
Ting et al.

(10) Patent No.: US 7,700,929 B2
(45) Date of Patent: **\*Apr. 20, 2010**

(54) REMOTE LASER ASSISTED BIOLOGICAL AEROSOL STANDOFF DETECTION IN ATMOSPHERE

(75) Inventors: Antonio Ting, Silver Spring, MD (US);
Ilya Alexeev, West Chester, PA (US);
Phillip Sprangle, Great Falls, VA (US);
Richard Hubbard, Burke, VA (US);
Glenn Rubel, Baldwin, MD (US);
Eldridge Briscoe, San Diego, CA (US);
Christopher Moore, Prince Frederick, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/407,429

(22) Filed: Mar. 19, 2009

(65) Prior Publication Data
US 2009/0184258 A1  Jul. 23, 2009

Related U.S. Application Data

(62) Division of application No. 11/467,580, filed on Aug. 28, 2006, now abandoned.

(51) Int. Cl.
*G01N 21/64* (2006.01)

(52) U.S. Cl. .................... 250/461.1; 250/461.2
(58) Field of Classification Search ............. 250/461.1, 250/461.2
See application file for complete search history.

(56) References Cited

U.S. PATENT DOCUMENTS

2002/0175294 A1\* 11/2002 Lee et al. ............... 250/458.1
2003/0147119 A1\* 8/2003 Samson ...................... 359/326

OTHER PUBLICATIONS

Alexeev et al.,"Longitudinal compression of short laser pulses in air", Applied Physics Letters, May 17, 2004, vol. 84, No. 20, pp. 4080-4082.\*

\* cited by examiner

*Primary Examiner*—David P Porta
*Assistant Examiner*—Mindy Vu
(74) *Attorney, Agent, or Firm*—John J. Karasek; Stephen T. Hunnius

(57) ABSTRACT

A system for detecting atmospheric contamination, the system comprising a laser operable to generate an infrared light beam comprising a longitudinal component and a transverse component, the laser remote from the atmospheric contamination, and a processor operable to process a flouresence resulting from contact between the atmospheric contamination and an ultraviolet light being generated from the longitudinal and transverse components of the infrared light of the laser, wherein the processor determines the identity of the fluorescence by comparing the fluorescence to known fluorescence.

18 Claims, 3 Drawing Sheets

REMOTE LASER ASSISTED BIOLOGICAL AEROSOL STANDOFF DETECTION IN ATMOSPHERE

This is a divisional application of U.S. patent application Ser. No. 11/467,580 filed on Aug. 28, 2006 the entirety of which is herein incorporated by reference.

A common method used to detect and identify biological substances suspended in air in the form of aerosols or clouds involves air sample collection in the field and their subsequent analysis in mobile laboratories. While this approach can be acceptably accurate, it has many disadvantages. Among these disadvantages includes being dangerous to personnel conducting the tests as they are exposed to hazardous biological agents. In addition, transporting the test equipment to the testing site can be difficult, especially if the test site is remote and/or in harsh terrain. Furthermore, the testing can be time-consuming in order to test large areas, thus decreasing the value of the testing by delaying obtaining the test results.

An alternative method for the remote sensing of biological substances, for example, would be a standoff detection such as a LIDAR (light detection and ranging) using an UV laser source. LIDAR technology employs laser pulses to determine the distance to an object or surface, for example. Backscattered fluorescence signals from the laser pulses encountering objects or materials indicates the presence and the location of any potential microscopic biological materials. The characteristic spectral information may also enable identification of these potential microscopic biological materials. However, there are still problems associated with this method. Employing a LIDAR system causes many molecules of interest to be directly excited by radiation in the vacuum ultraviolet (VUV) region, which, unfortunately, is heavily absorbed by the Earth's atmosphere for wavelengths below 300 nm. Thus, limiting the UV LIDAR detection range to only a few hundred meters, especially in high ozone urban environment.

BRIEF SUMMARY OF THE INVENTION

To overcome the limited UV LIDAR detection range, a locally generated UV radiation excitation source is preferred. This source is preferably placed at a remote location, instead of launching an intense UV laser from a distance. Generating the UV radiation at a remote location, directed towards the atmospheric contaminant through nonlinear processes associated with propagation of intense laser pulses, is preferable.

Accordingly, one object of an embodiment of the present invention is the ability to test for contamination from a remote location from the contaminant site.

Another object of an embodiment of the present invention is the ability to obtain real-time test results for an area of contamination.

These and other objects are achieved by an embodiment of the present invention including a method for detecting atmospheric contamination including generating a light beam directed toward the atmospheric contamination, wherein the light beam originates remotely from the atmospheric contamination, and then modulating the light beam, as the light beam travels through the atmosphere, in order to generate ultraviolet light within an area of the atmospheric contamination, detecting flouresence within the area of the atmospheric contamination, when the generated ultraviolet light contacts the atmospheric contamination; and comparing the detected flouresence signatures of known atmospheric contaminants, to determine the atmospheric contaminant.

BRIEF DESCRIPTION OF THE DRAWINGS

These and other objects, advantages, and novel features will be more readily appreciated from the following detailed description when read in conjunction with the accompanying drawings, in which.

DETAILED DESCRIPTION OF THE INVENTION

An embodiment of the present invention includes a remote detector of biological aerosols that employs broad bandwidth laser pulses at atmospheric transmitting wavelengths such as infrared (IR). The detector delivers laser pulses from a remote location to the contaminated site via locally generated UV radiation, through the process of light filament formation and atmospheric breakdown. The generated UV radiation is used as the light source to excite fluorescence in the contaminated area containing contaminants such as biological substances. The fluorescent response is processed, via a processor, to map out the contaminated area and identify the contaminating agent.

Figure 1:
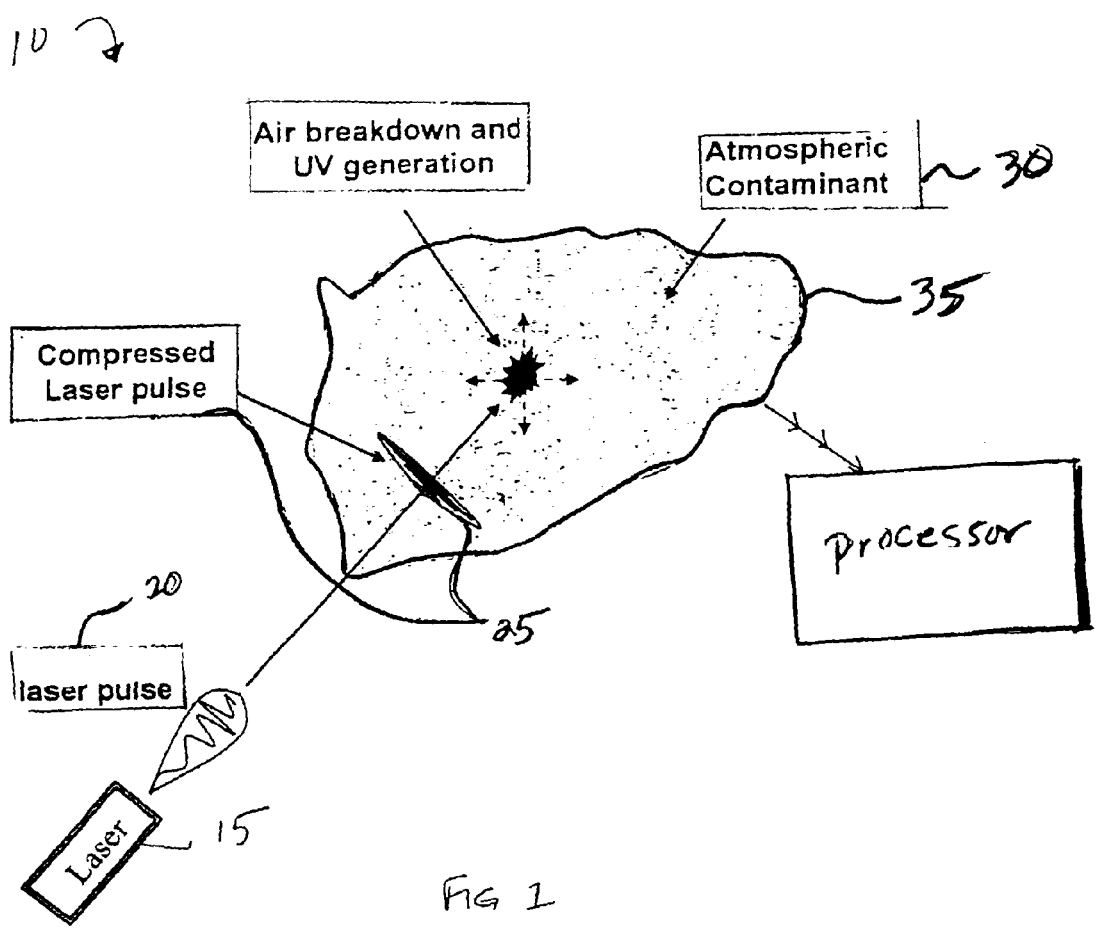
FIG. 1 is illustrative of a block diagram of an embodiment of the present invention.

FIG. 1 depicts a system 10 for remote detection of air contaminants, for example biological aerosols. The detection system employs a laser 15 which emits a laser pulse 20, typically in the infrared (IR) range from about 700 nm.-10,000 nm. This initial pulse 20 is preferably frequency chirped, with the wavelength and the frequency being a function of time. The chirped pulse can be generated by optical grating-based dispersion such as that occurring in a chirped pulse amplifier laser, or by any suitable method. The laser pulse 20 comes into contact with the air which acts to compress the laser pulse 20 into a compressed laser pulse 25, typically in the ultraviolet (UV) range. More specifically, the laser pulse 20 is linearly compressed in a longitudinal direction thus increasing the power of the laser pulse 20. In addition, the laser pulse is non-linearly focused in a transverse direction resulting in a higher laser intensity or, in other words, higher power/unit area. The present invention employs a compressed laser pulse 25 which implicitly refers to a longitudinally compressed and transversely focused laser pulse.

A feature of an embodiment of the present invention includes employing a laser pulse in the IR spectrum, because upon compression, as described above, the laser is able to achieve a higher laser intensity thus allowing the laser source to be remote, approximately 4 km., from the contamination site. Accordingly, although the initial source is IR after compression the laser pulse results in a UV spectrum laser (less than 300 nm.) which is then converted to the visible range approximately 330-700 nm. This concept is discussed in detail below.

Once the linear and non-linear components of the compressed laser pulse come into contact with the atmospheric contaminants 30, the contaminants fluoresce in the area of contamination 35. This information is then sent to processors, via sensors (not shown), for example, so the information collected about the offending contaminants at the remote site is compared to known signatures of biological contaminants to determine the identity of the offending contaminant.

The non-linear transverse focusing results in laser filaments as discussed below.

The compressed laser pulse comprises an ultraviolet laser pulse further comprising three components including a self-phase modulated laser pulse spectrum, a third harmonic of the laser pulse (at one-third the wavelength of the IR laser, i.e., 267 nm for an IR wavelength of 800 nm.), and a plasma radiation spectrum from the recombination of electrons and partially ionized air to produce a plasma that exists for a short duration. This plasma is readily recombined. This short duration plasma is produced when electrons are stripped from atoms to form ions, the electrons are then recombined with the available atoms within the ionized air by the intense compressed laser pulse and the electrons.

Among the three components mentioned above, the third harmonic of the laser pulse is a preferable marker for examining potential contaminants. Specifically, the third harmonic offers benefits including the fact that a significant number of biological markers have been shown to fluoresce under the third harmonic, such as tryptophan because these biological markers exist at the third harmonic. In addition, the third harmonic is a more dominating mechanism for generating UV spectrum because the third harmonic can be a coherent generation through phase matching. The third harmonic is also more efficient in exciting the biological markers due to the fact that the third harmonic has higher spectral intensity when compared to the narrower spectral bandwidth.

In order to achieve appropriate control of the laser pulse formation and air breakdown, an embodiment of the present invention allows adjustment of the initial laser pulse parameters such as laser placement with respect to contamination area, pulse energy, beam size, beam divergence, pulse duration, and frequency chirp (arrangement of frequency components along the pulselength). The group velocity dispersion (GVD) parameter of air, $\beta_2$, which is proportional to the rate of change of group velocity of light with wavelength, is positive in the optical and near IR regions. This means that light with longer wavelengths travels faster than light with shorter wavelengths. For a pulse with a negative frequency chirp where shorter wavelengths are at the beginning and longer wavelengths are at the end, it will compress longitudinally as the different wavelength components catch up with one another. For a pulse in which frequency is a linear function of time, the propagation distance for maximum longitudinal pulse compression, $L_{GVD}$, is approximately $$\frac{2T(0)}{\beta_2 \delta\omega},$$

where T(0) is the initial laser pulse duration and $\delta\omega$ is the frequency bandwidth of the laser. Therefore, by tailoring the initial laser pulse bandwidth and pulse length, $L_{GVD}$ can be appropriately selected.

As the pulse is shortened, the power increases, as discussed above. There is a threshold power level given by $P_{crit}=\lambda^2/2\pi n_0 n_2$, above which nonlinear optical effects are induced, where $n_0$ is the linear index of refraction, and $n_2$ is the nonlinear index of refraction. For light with $\lambda=800$ nm, $P_{crit}\approx 1.7$ gigawatts in air. At these and higher power levels, the refractive index across the transverse profile of the laser beam is no longer uniform and causes the beam to self-focus. The non-uniformity is with respect to the refractive index of air. The refractive index of air is normality a constant, and varies with density and temperature. Accordingly, in the small transverse cross-sectional area where the laser beam passes through, the air is uniform and constant. However, for a high enough laser intensity, the refractive index is not uniform. The refractive index of air is non=-uniform transversely due to the high intensity laser. This is a consequence of the nonlinear nature of the refractive index.

The characteristic distance for a transverse non-linear self-focusing (NSF) is given by $$L_{NSF} = \frac{z_R}{\sqrt{\frac{P(z)}{P_{crit}} - 1}},$$

where $z_R = \frac{\pi n_0 R^2}{\lambda}$ is the Rayleigh range, and R is the beam radius. The transverse self-focusing range, $L_{NSF}$, can then be selected by choosing the correct initial beam size, R, and initial beam power, P(0). For a properly chosen set of parameters the focal distances for the linear longitudinal compression and the transverse non-linear focusing can be made to coincide, which results in a significant increase in the laser intensity over a relatively localized region and the onset of atmospheric breakdown (and plasma formation) from the increased laser intensity at the desired location occurs. This approach controls the location of the atmospheric breakdown and the UV radiation generation that follows.

Longitudinal pulse compression in air occurs for a negatively chirped laser pulse (frequency decreases in time). This is because air has a normal (positive) GVD such that high frequency components travel at slower velocities. The back of the negatively chirped laser pulse, which is composed of the lower frequencies, travels faster than the front and eventually catches up and shortens the pulse length. In a low intensity regime, where nonlinear effects do not significantly affect the temporal shape of the pulse, and assuming Gaussian temporal profile the pulse duration T can be written as a function of the propagation distance z $$T(z) = T_0\left(\left(1+\beta_0\frac{z}{Z_T}\right)^2 + \left(\frac{z}{Z_T}\right)^2\right)^{1/2} \quad (3)$$

where $T_0$ is the initial pulse duration (FWHM), $\beta_0$ is the initial pulse chirp, and $Z_T=T_0^2/(4\ln 2\beta_2)$ is the group velocity dispersion length.[7] The GVD parameter, $\beta_2$, for atmospheric air is usually estimated by the updated Edlén equation.[8] The calculated value of $\beta_2$ is ~21 fs$^2$/m for typical experimental parameters of air such as a temperature around 20 degrees Celsius, a 50% relative humidity, and a laser wavelength of ~800 nm. If the laser pulse is initially negatively chirped ($\beta_0<0$), it will be compressed as it propagates through the atmosphere until it reaches the minimum pulse length of $T_0/(1+\beta_0^2)^{1/2}$ at the distance $$z_s = -\frac{\beta_0}{1+\beta_0^2}Z_T.$$

It has been experimentally shown that low energy negatively chirped laser pulses can be successfully compressed after propagating in air for a relatively long distance, in good agreement with the linear model. At higher energy levels, temporal pulse shaping can be significantly affected by nonlinear effects such as the self-phase modulation (SPM), but can be potentially controlled through spectral and temporal pulse shaping.

For laser parameters such as a frequency chirp of $\beta_0 = \sim 0.025$ (corresponding to a bandwidth of 20 nm for a 800 nm Ti:Sapphire laser) and an initial laser pulse length of 4.83 psec, the distance at which the laser pulse will be compressed to a 50 fsec pulse is 10 km. Laser filaments are formed when the IR laser pulse is transversely focused resulting in UV radiation generation. Specifically, in high power ultrashort laser pulse propagation in air there is a dynamic balance between the nonlinear self-focusing from the air and the defocusing from the laser-induced plasma, which forms as the laser ionizes the air and happens before recombination occurs. Ionization is the separation of electrons from atoms. This occurs when high intensity laser radiation interacts with atoms. Ions are formed when electrons are stripped from the atoms. Recombination occurs when the electrons recombine with the ions to re-form the atoms, once a laser pulse has been emitted and a plasma has formed, and is in the process of cooling. The energy released during this recombination process shows up as a light and is called the recombination radiation. This radiation has different wavelength spectrums for different atoms and laser intensities. With respect to an embodiment of the present invention, the recombination radiation spectrum is in the ultra-violet range.

This results in a breakup of the laser beam into one or several filaments of about 100 μm in diameter that propagates over distances of several meters. Each filament contains a very high intensity core of about $10^{13}$ W/cm$^2$, which, in addition to generating broadband white-light continuum ranging from the UV to the mid IR regions, converts part of the fundamental frequency to the 3$^{rd}$ harmonic. Currently available high peak power ultrashort lasers usually operate in the near IR region around 700-10,000 nm, thus placing the 3$^{rd}$ harmonic in the range of between 233 nm and 300 nm.

Figure 2:
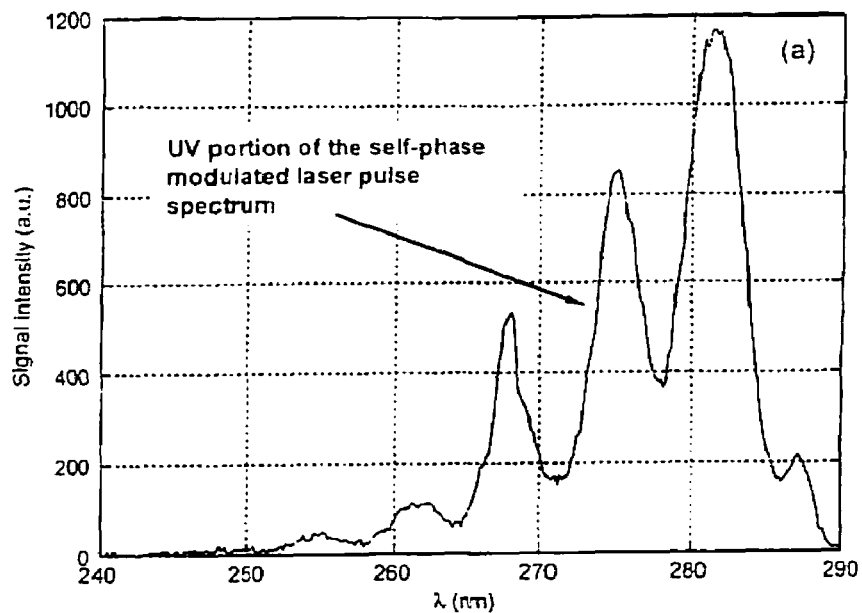
FIG. 2 is a graph illustrating the UV portion of the self-phase modulated spectrum of the laser beam containing filaments.
Figure 3:
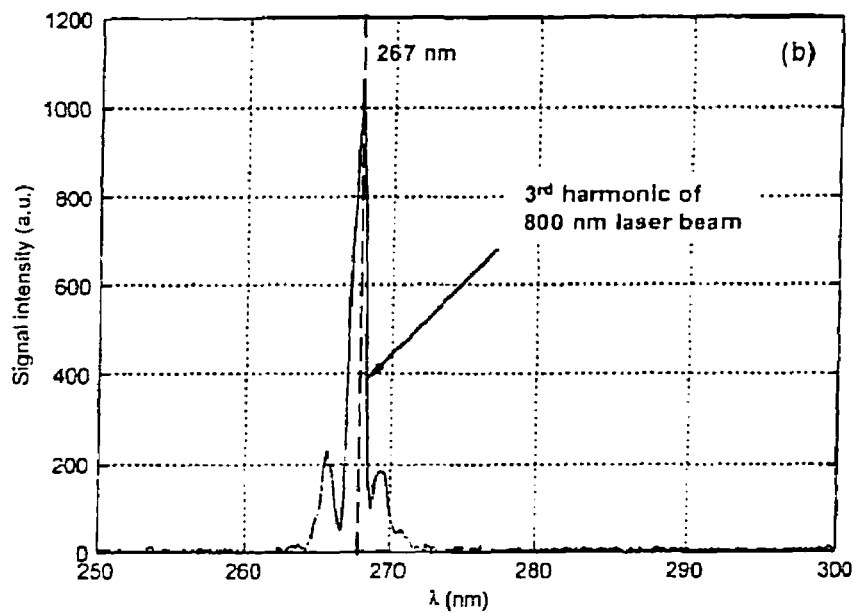
FIG. 3 is a graph illustrating the spectrum of a third harmonic of the fundamental frequency.

FIG. 2 illustrates an example of the UV portion of the self-phase modulated spectrum of the laser beam containing laser filaments. FIG. 3 illustrates the spectrum of the third harmonic of the fundamental frequency. The central wavelength of the initial laser spectrum was approximately 800 nm. Ultraviolet radiation can be generated in air by an intense laser pulse such as the compressed short infrared laser pulse described in this invention. The generation processes involve nonlinear interactions between the intense laser radiation with the air. The nonlinearity originates from the change of the refractive index of air as a function of laser intensities. For a short intense laser pulse with finite lateral extension, the intensity changes rapidly both in time (from front to back of pulse) as represented by non-linear transverse compression and in space (more intense along the laser axis) as represented by the linear longitudinal compression.

Three processes primarily contribute to the UV production from the IR laser source. These processes include third harmonic generation, self-phase modulation and recombination of electrons to produce a temporary, or short duration plasma.

Harmonic generation produces overtones of the fundamental as the electrons bound to the air molecules oscillate in the intense field of the laser and execute non-sinusoidal orbits. In air, the strongest emission is the third harmonic. For a short pulse laser with a fundamental wavelength of 800 nm, the third harmonic has a wavelength of 267 nm which is ultraviolet. This is shown in FIG. 3.

Self-phase modulation produces broad band radiation that extends into the UV spectral region through the temporal variation of the laser phase as the laser intensity varies within the pulse. This is shown in FIG. 2.

Finally, ionization and recombination produces UV line emission and broadband radiation as the photo-ionized atoms reabsorb the electrons and release the energy. These UV radiations constitute the UV sources for exciting fluorescence in the atmospheric contaminants at a distance.

The dominance or suppression of one or more of the three processes can be conveniently controlled by tailoring the outgoing infrared laser pulse from the short pulse laser. For example, a change in the pulse shape could enhance one process over the other. That could include varying the final compressed pulse length by adjusting the initial frequency bandwidth of the laser, altering the frequency chirping in the laser pulse, and incorporation of additional geometrical focusing optics in the output beam director, among others. A desired UV spectrum with the appropriate UV spectral lines can therefore be generated by manipulating the parameters and configuration of the IR short pulse laser. Most of these parameters can be adjusted in real time. The other parameters can be preloaded and pre-adjusted for different applications and suspected contaminants in the target area.

Figure 4:
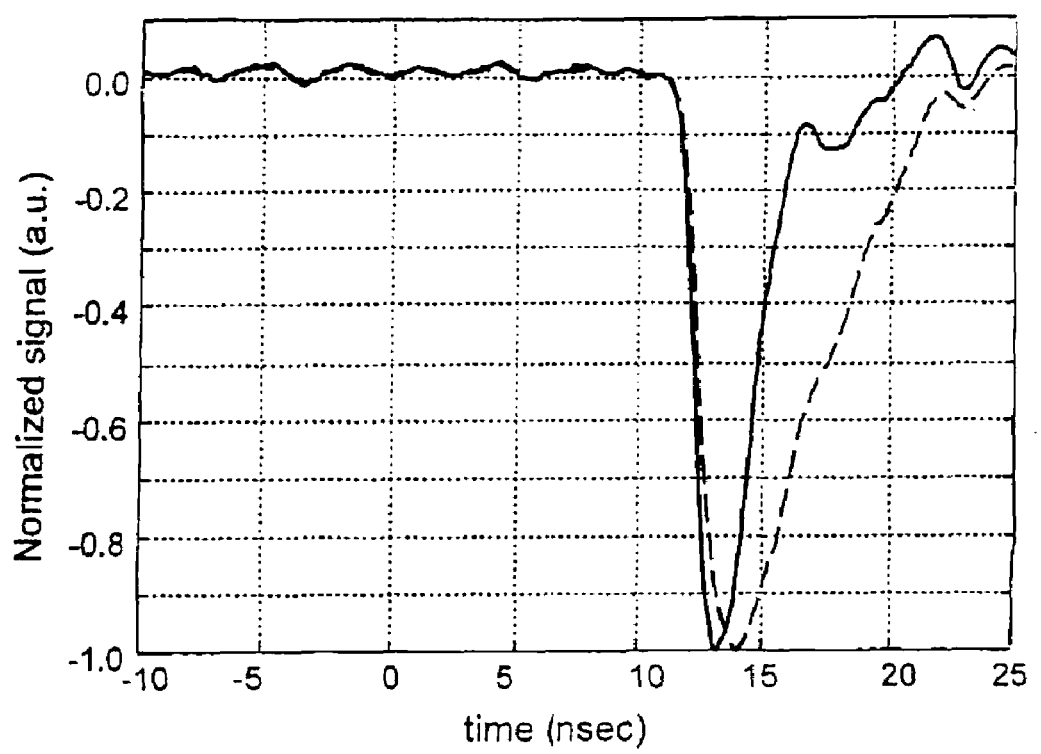

FIG. 4 shows one of the detection and identification methods that can be applied for the UV induced fluorescence signature. It is applicable to the biological stimulant (albumin powder). The decay lifetime of the fluorescence from the albumin powder is a signature that can be picked up through the use of time resolved spectroscopy. This technique is one among several spectroscopic methods of detecting contaminants through their UV induced fluorescence.

Typical energy conversion efficiency to UV region is around $10^{-4}$-$10^{-3}$, which makes laser filaments quite a promising source of locally generated UV light. By positioning the laser filaments in the area of interest and registering the fluorescent response from this region, the detection and identification of biological aerosols can be conducted. The major advantage of this method is its capability to position the source of UV radiation at the desired location through controlling the filament formation. Since the air absorption and scattering of the laser wavelength in the near infrared region is relatively weak the scanning range will not be limited as in the case of a direct UV laser source. These filaments can be generated as far as several to over ten kilometers away from the laser. In addition, the relatively short length of the filament (on the scale of about ten meters) can allow ranging of the contaminated area with good spatial resolution.

Often, the fluorescent spectroscopic signature of the biological agent overlaps with the broadband white light continuum generated by the short pulse in air. These spectra can be distinguished by making time-resolved spectral measurements. As long as the duration of the laser pulse is much shorter than the characteristic decay time of the biological fluorescence, these spectral signals can be time resolved. Typical fluorescent decay time is at least a few nanoseconds long, while the typical laser pulse used in this invention is usually shorter than 1 picosecond at the final air breakdown location. By using fast sensing detectors, the spectral signal from the scattered laser light can be separated from the fluorescent response. As an example, FIG. 4 shows the time resolved signal from a photo multiplier tube (PMT) for fluorescent (dashed line) and non fluorescent (solid line) aerosols at the wavelength of interest (340 nm). The difference in these temporal profiles in the PMT signal allows for the detection of the biological agent dispersed in air.

The major advantages of an embodiment of the present invention is the operation of UV fluorescence lidar using atmospheric propagating laser wavelengths and the control of the location of the UV radiation generation through laser pulse chirping and beam collimation. The data can be accumulated in real time thus allowing the sampling of large contaminated areas. The lasers and the detectors required for this application are typically commercially available.

Alternatives to an embodiment of the present invention can be made at the laser and on the methodology. Alternative wavelengths are available for the ultrashort femtosecond laser used in this invention depending on the laser gain materials. At the 700-900 nm region. Titanium Sapphire can be used. At the 1050 nm region, Neodymium glass and Ytterbium Tungstate laser can be used. At the 1550 nm region, Erbium fiber lasers and optical parametric chirped pulsed amplifier (OPCPA) lasers can be used. The 1550 nm wavelength has the added advantage of being "eye-safe". These lasers all have enough bandwidth to be compressed by the atmosphere to deliver an ultrashort high power laser pulse at a remote distance to cause filament development and atmospheric breakdown. Another alternative of generating different initial wavelengths is to frequency double the fundamental wavelengths before the laser pulse is transmitted through the atmosphere. For example, 530 nm femtosecond laser pulses can be obtained by frequency doubling a 1050 nm ultrashort laser using the appropriate frequency doubling nonlinear crystal. Similarly, other frequencies such as 400 nm and 775 nm can be obtained by frequency doubling the 800 nm and 1550 nm lasers. Therefore, limited tenability can be obtained to tailor to the required wavelength for the specific chemical or biological compound in question.

The mechanisms for generating the required UV radiation by the filaments and atmospheric breakdown can have alternatives, in addition to the white-light super-continuum and third harmonic generation, such as higher order harmonic generations appropriate for the associated fundamental wavelengths of the lasers. For example, the fifth harmonic generation is appropriate for the 1050 nm fundamental and the seventh harmonic generation is appropriate for the 1550 nm fundamental for generation of UV in the 200 nm region. Efficient high order harmonic generation can be achieved by appropriate shaping of the outgoing laser pulse through bandwidth manipulating elements in the laser.

The method of biological agent detection also is not limited to UV induced fluorescence only. Biological agents are also known to produce fluorescence when illuminated with other laser wavelengths such as 530 nm which is available as a frequency doubled 1050 nm laser as described in the previous paragraphs. Other methods of detection that utilize nonlinear interaction of the laser pulse with the biological compound are also available. For example, two-photon-excitation where two photons are required to cause fluorescence can be used as proposed in reference [4], where the fundamental wavelength was suggested to be 530 nm to cause fluorescence that could otherwise be generated at the UV wavelength of 265 nm. An embodiment of the present invention will either generate the 530 nm wavelength with the appropriate laser for the two-photon excitation, or to produce the needed 265 nm UV light at the remote location using third harmonic with a Titanium Sapphire laser at 795 nm.

Another alternative to the laser configuration is the repetition rate of the laser. Most standoff detection schemes can benefit from high repetition rate data collection so that the signal to noise ratio can be improved through statistical data analysis. However, there are instances where single shot high energy per pulse laser can be useful also.

Although only several exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for detecting atmospheric contamination, said system comprising:
   a laser operable to generate an infrared light beam comprising a longitudinal component and a transverse component, said laser remote from the atmospheric contamination; and
   a processor operable to process a fluorescence resulting from contact between the atmospheric contamination and an ultraviolet light being generated from the longitudinal and transverse components of the infrared light of the laser;
   wherein the longitudinal component of said infrared light beam is linearly compressed and increases the intensity of said infrared light beam;
   wherein said processor determines the identity of the fluorescence by comparing the fluorescence to known fluorescence.

2. The system for detecting atmospheric contamination of claim 1 wherein ultraviolet light is generated by non-linearly compressing a transverse component of said infrared light beam and converting said non-linearly compressed transverse component to an ultraviolet light beam.

3. The system for detecting atmospheric contamination of claim 1 further comprising:
   a detector to detect said fluorescence of the atmospheric contaminants via sensors.

4. The system for detecting atmospheric contamination of claim 3 wherein the detected fluorescence in the ultra-violet range includes detecting the fluorescence within the wavelength of approximately 330 nm-700 nm.

5. The system for detecting atmospheric contamination of claim 3 further including comparing decay lifetime of the atmospheric contaminants to the decay lifetime of known contaminants.

6. The system for detecting atmospheric contamination of claim 1 wherein said generated ultraviolet light beam includes generating a self-phase modulated spectrum of the ultraviolet light beam.

7. The system for detecting atmospheric contamination of claim 1 wherein said generated ultraviolet beam includes generating a spectrum of the third harmonic of a fundamental frequency of the ultraviolet light beam.

8. The system for detecting atmospheric contamination of claim 1 wherein said generated ultraviolet light beam includes recombining electrons with ionized air to form short duration plasma.

9. The system for detecting atmospheric contamination of claim 1 wherein said generated infrared light beam is an infrared light beam having a wavelength of approximately 700 nm-10,000 nm.

10. A system for detecting atmospheric contamination comprising:
    an infrared light beam wherein said infrared light beam is generated remotely from the atmospheric contamination;
    an infrared light beam wherein said infrared light beam is directed toward the atmospheric contamination;

wherein a longitudinal component of said infrared light beam is linearly compressed and the intensity of said infrared light beam is increased;

wherein a transverse component of said infrared light beam is non-linearly compressed;

wherein said non-linearly compressed transverse component is convened to an ultraviolet light beam;

a detector for detecting the fluorescence of the atmospheric contamination that is produced when said generated ultraviolet light contacts the atmospheric contamination; and a processor that determines the identity of the fluorescence.

11. The system for detecting atmospheric contamination of claim 10 further comprising a detector which detects said fluorescence of the atmospheric contaminants via sensors.

12. The system for detecting atmospheric contamination of claim 10 wherein said generated ultraviolet light beam includes a generated self phase modulated spectrum of the ultraviolet light beam.

13. The system for detecting atmospheric contamination of claim 10 wherein said generated ultraviolet beam includes a generated spectrum of the third harmonic of a fundamental frequency of the ultraviolet light beam.

14. The system for detecting atmospheric contamination of claim 10 wherein said generated ultraviolet light beam includes recombined electrons with ionized air to form short duration plasma.

15. The system for detecting atmospheric contamination of claim 10 wherein said generated infrared light beam has a wavelength of approximately 700 nm-10,000 nm.

16. The system for detecting atmospheric contamination of claim 10 wherein said detected fluorescence in the ultraviolet range includes detected fluorescence within the wavelength of approximately 330 nm-700 nm.

17. The system for detecting atmospheric contamination of claim 10 wherein said detected fluorescence is compared with signatures of known atmospheric contaminants to determine the atmospheric contaminant.

18. The system for detecting atmospheric contamination of claim 10 wherein the decay lifetime of the atmospheric contaminants is compared to the decay lifetime of known contaminants.

* * * * *